United States Patent
Kargar et al.

(10) Patent No.: US 8,379,793 B2
(45) Date of Patent: Feb. 19, 2013

(54) SYSTEM FOR POSITIONING AND X-RAY IMAGING A HEART

(75) Inventors: Soroosh Kargar, Lake in the Hills, IL (US); Weng Lei, Mount Prospect, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 233 days.

(21) Appl. No.: 13/043,713

(22) Filed: Mar. 9, 2011

(65) Prior Publication Data

US 2011/0293065 A1 Dec. 1, 2011

Related U.S. Application Data

(60) Provisional application No. 61/350,072, filed on Jun. 1, 2010.

(51) Int. Cl.
*G01N 23/04* (2006.01)
(52) U.S. Cl. .......................... 378/62; 378/98; 378/98.12
(58) Field of Classification Search ................... 378/62, 378/98, 98.11, 98.12; 382/128–132
See application file for complete search history.

(56) References Cited

U.S. PATENT DOCUMENTS

2009/0010516 A1  1/2009  Boese et al.

OTHER PUBLICATIONS http://en.wikipedia.org/wiki/Thoracis_vertebrae, web site, printed Feb. 16, 2011.

*Primary Examiner* — Courtney Thomas
(74) *Attorney, Agent, or Firm* — Alexander J Burke

(57) ABSTRACT

A system positions a patient for X-ray imaging of a Left Atrium of a heart, using an imaging system for, acquiring data representing a frontal first X-ray image and representing a lateral second X-ray image of a patient. A display processor initiates generation of data representing a first composite display image including the first X-ray image and a first graphical overlay for aligning with vertebra in the first X-ray image. The display processor initiates generation of data representing a second composite display image including the second X-ray image and a second graphical overlay for aligning with vertebra in the second X-ray image. The imaging system is positioned for imaging a heart left atrium in response to movement of a table supporting the patient to align the first graphical overlay with the vertebra in the first X-ray image and to align the second graphical overlay with the vertebra in the second X-ray image.

14 Claims, 17 Drawing Sheets

SYSTEM FOR POSITIONING AND X-RAY IMAGING A HEART

This is a non-provisional application of provisional application Ser. No. 61/350,072 filed 1 Jun. 2010, by S. Kargar et al.

FIELD OF THE INVENTION

This invention concerns a system for positioning a patient for X-ray imaging of a Left Atrium of a heart using graphical overlays on X-ray images acquired in frontal and lateral positions for aligning the images with vertebra, for example.

BACKGROUND OF THE INVENTION

In order to acquire a 3D image of the left atrium using a rotational angiography system, it is necessary to position the left atrium at iso-center of the angiography system. The placement of a left atrium at iso-center for imaging ensures that the region of interest (i.e. left atrium) does not drift out of a displayed field of view. Known systems involve use of a catheter placed in a left pulmonary artery that is positioned anterior to a left atrium. In the known systems iso-centering of a Left Atrium of a heart in the frontal position is performed by an operator under fluoroscopy (live reduced dose X-ray imaging) moving a patient support table horizontally until the spinal vertebrae are about 1.5 cm on the left of the image center line and by moving the table longitudinally until the catheter that was positioned in the left pulmonary artery is placed at the top of the image. Iso-centering in the lateral position is performed by an operator moving the support table up or down until two thirds of the vertebrae body is visible on the right of the image. This is a slow and inaccurate procedure involving substantial risk in placing of a catheter. A system according to invention principles addresses this deficiency and related problems.

SUMMARY OF THE INVENTION

A System centers a left atrium of a heart, for example, without requiring invasive insertion of a catheter for use in locating the left atrium or other structures. A system positions a patient for X-ray imaging of a Left Atrium of a heart, using an imaging system for, acquiring data representing a first X-ray image of a patient in a substantially frontal position and acquiring data representing a second X-ray image of a patient in a substantially lateral position. A display processor initiates generation of data representing a first composite display image including the first X-ray image and a first graphical overlay for aligning with vertebra in the first X-ray image. The display processor initiates generation of data representing a second composite display image including the second X-ray image and a second graphical overlay for aligning with vertebra in the second X-ray image. The imaging system is positioned for imaging a heart left atrium in response to movement of a table supporting the patient to align the first graphical overlay with the vertebra in the first X-ray image and to align the second graphical overlay with the vertebra in the second X-ray image.

DETAILED DESCRIPTION OF THE INVENTION

A System centers a left atrium of a heart, for example without requiring invasive insertion of a catheter for use in locating the left atrium or other structures. Specifically, the system eliminates a need for placing a catheter in the left pulmonary artery as a marker by displaying a graphical display of a vertebrae model on an imaging monitor during iso-centering of a left atrium. An imaging system operator moves a patient support table horizontally and longitudinally and superimposes the patient vertebrae in an image with the graphical display of vertebrae on an imaging monitor in frontal position, for example. A $5^{th}$ thoracic vertebra is located posterior to the left atrium. The system advantageously performs iso-centering of the $5^{th}$ thoracic vertebra to iso-center the left atrium which is located in front of the $5^{th}$ thoracic vertebra. In lateral position, the system adjusts patient position by vertically moving a patient support table up or down until patient vertebrae in an image are superimposed by a vertebrae graphical element overlay displayed on an imaging system monitor.

Figure 5:
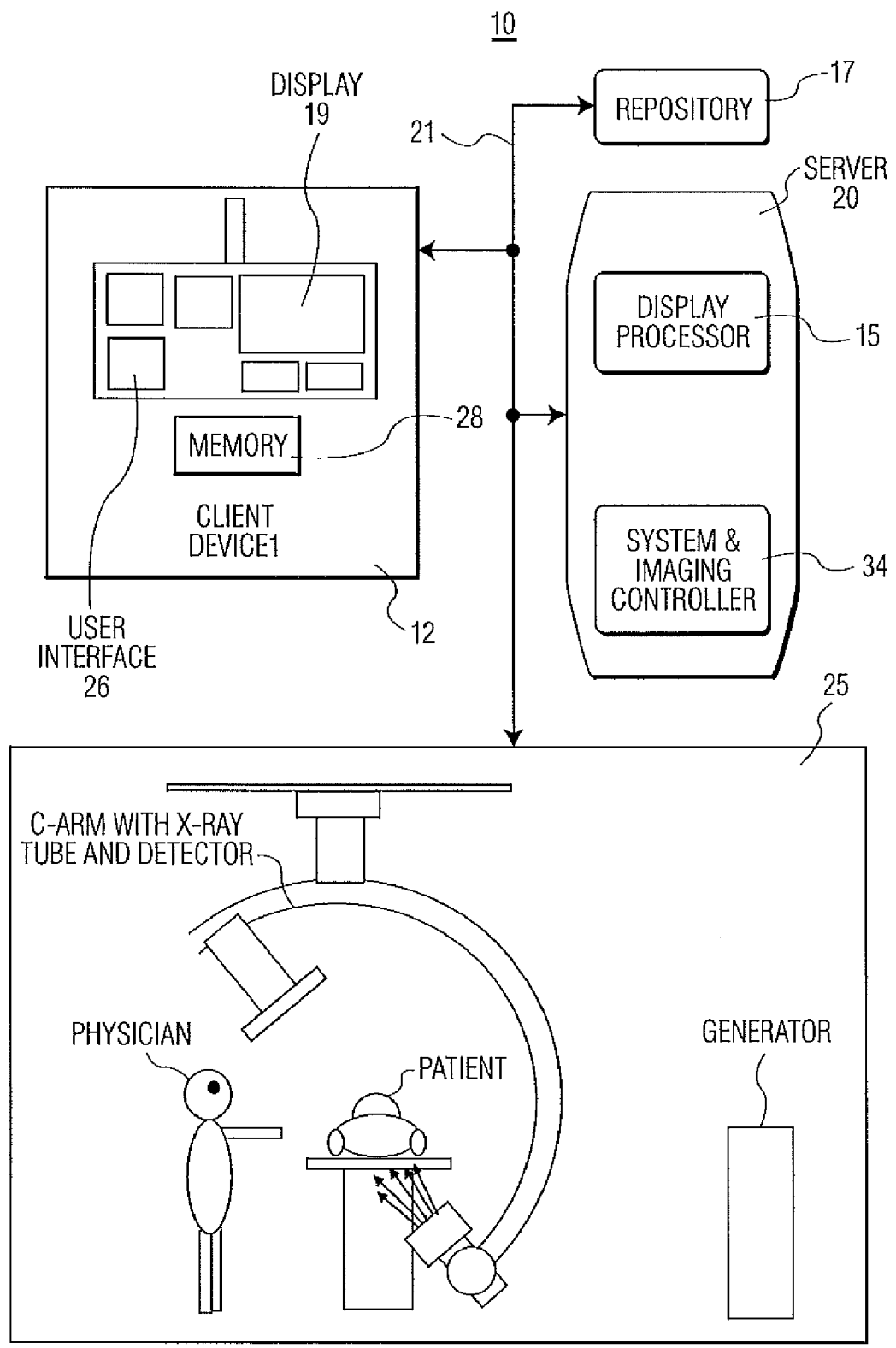
FIG. 5 shows a system for positioning a patient for X-ray imaging of a Left Atrium of a heart, according to invention principles.

FIG. 5 shows an Angiographic X-ray imaging system 10. System 10 includes one or more processing devices (e.g., workstations or portable devices such as notebooks, Personal Digital Assistants, phones) 12 that individually include a user interface control device 26 such as a keyboard, mouse, touchscreen, voice data entry and interpretation device, display 19 and memory 28. System 10 also includes at least one repository 17, X-ray imaging modality system 25 (which in an alternative embodiment may comprise an MR (magnetic resonance) or CT scan device, for example) and server 20 intercommunicating via network 21. X-ray modality system 25 for providing patient X-ray medical images, comprises a C-arm X-ray radiation source and detector device rotating about a patient table and an associated electrical generator for providing electrical power for the X-ray radiation system. The medical images are generated in response to predetermined user (e.g., physician) specific preferences. At least one repository 17 stores medical image studies for multiple patients in DICOM compatible (or other) data format.

A medical image study individually includes multiple image series of a patient anatomical portion which in turn individually include multiple images. Server 20 includes display processor 15 and system and imaging controller 34. Display 19 presents display images comprising a Graphical User Interface (GUI). Imaging controller 34 controls operation of imaging device 25 in response to user commands entered via user interface 26. In alternative arrangements, one or more of the units in server 20 may be located in device 12 or in another device connected to network 21.

System 10 positions a patient for X-ray imaging of a Left Atrium of a heart using imaging system 25. Imaging system 25 acquires data representing a first X-ray image of a patient in a substantially frontal position and acquires data representing a second X-ray image of a patient in a substantially lateral position. Display processor 15 initiates generation of data representing a first composite display image including the first X-ray image and a first graphical overlay for aligning with vertebra in the first X-ray image. Display processor 15 initiates generation of data representing a second composite display image including the second X-ray image and a second graphical overlay for aligning with vertebra in the second X-ray image. Imaging system 25 is positioned for imaging a heart left atrium in response to movement of a table supporting the patient to align the first graphical overlay with the vertebra in the first X-ray image and to align the second graphical overlay with the vertebra in the second X-ray image.

Figure 1:
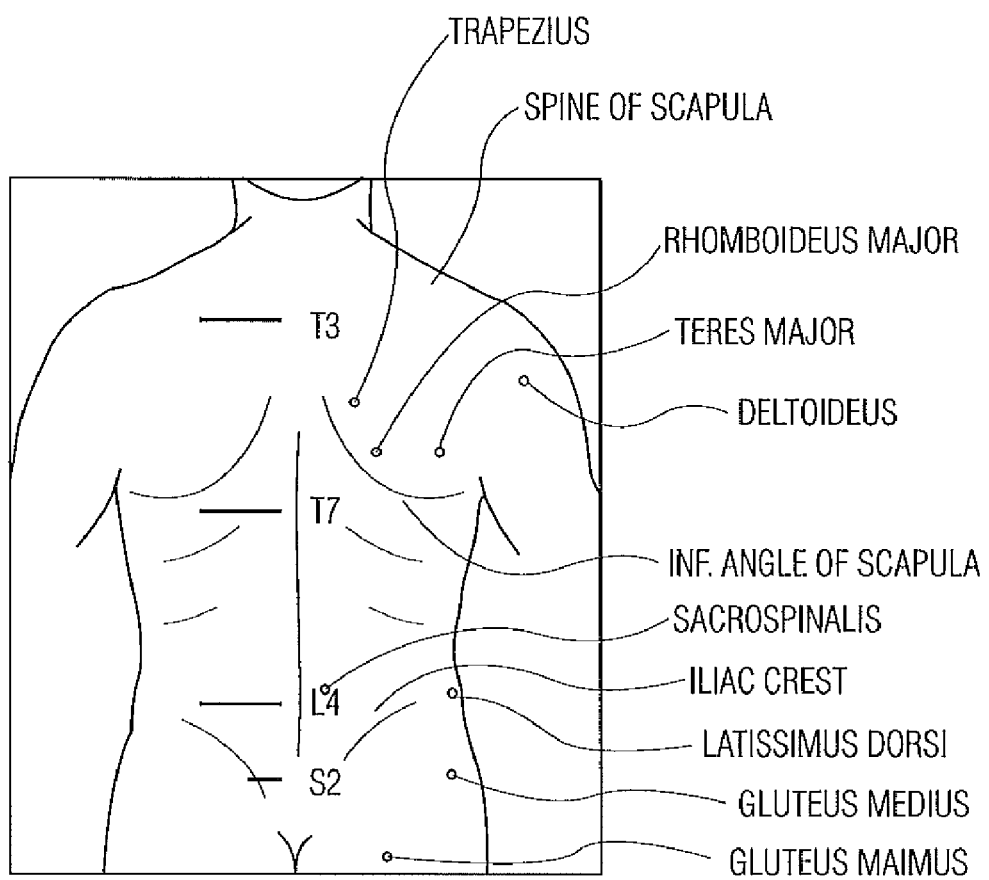
FIG. 1 shows orientation of a vertebral column on a patient body surface.
Figure 2:
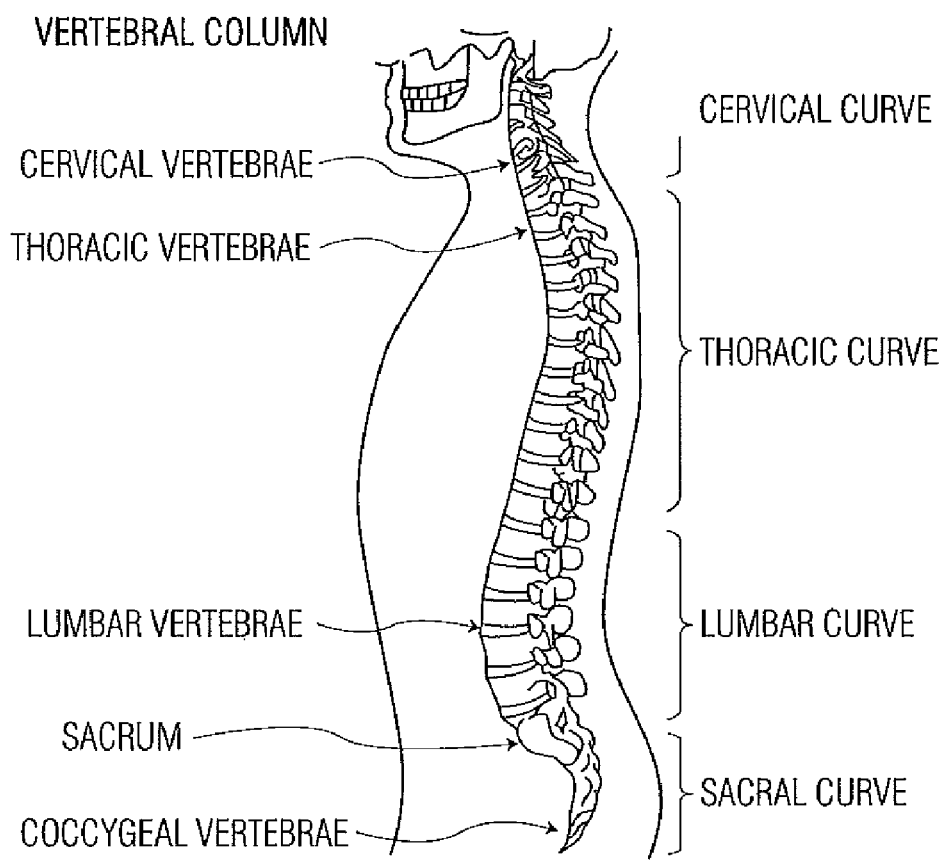
FIGS. 2 and 3 show a Vertebral Column
Figure 3:
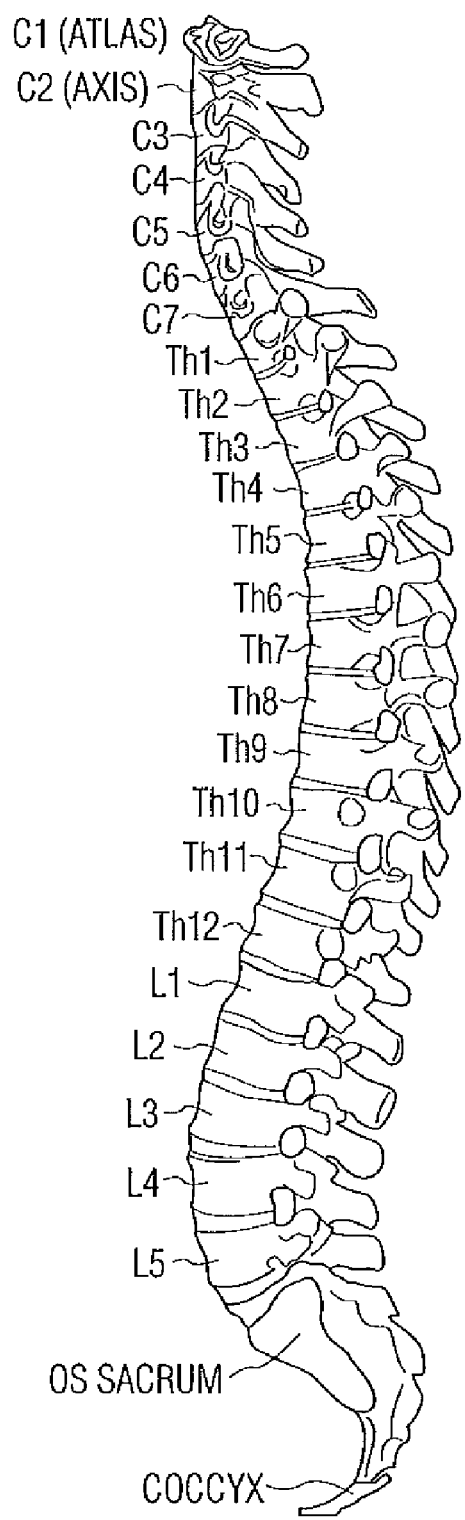
Figure 6:
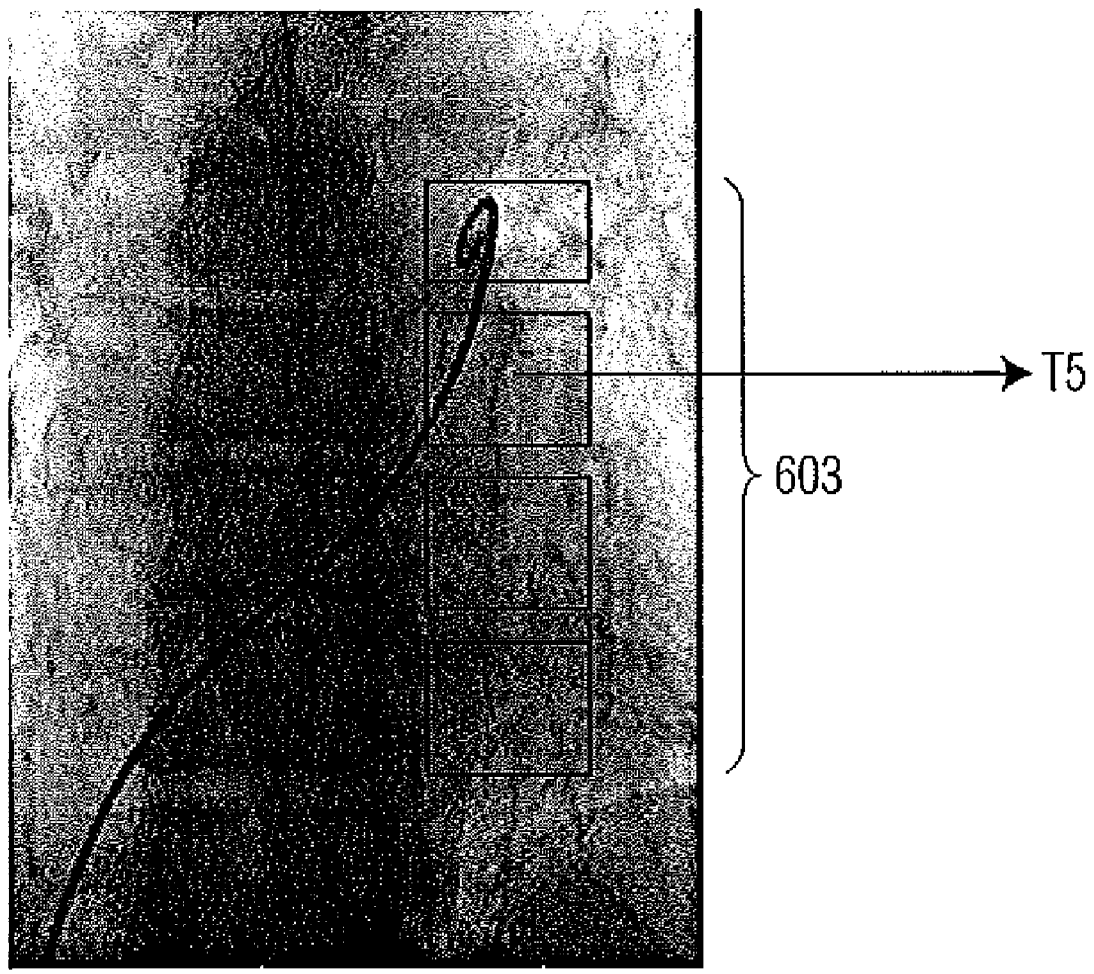
FIG. 6 shows a cardiac image including vertebrae and vertebrae overlay graphic elements for an anterior-posterior position prior to alignment of the overlay elements, according to invention principles.
Figure 7:
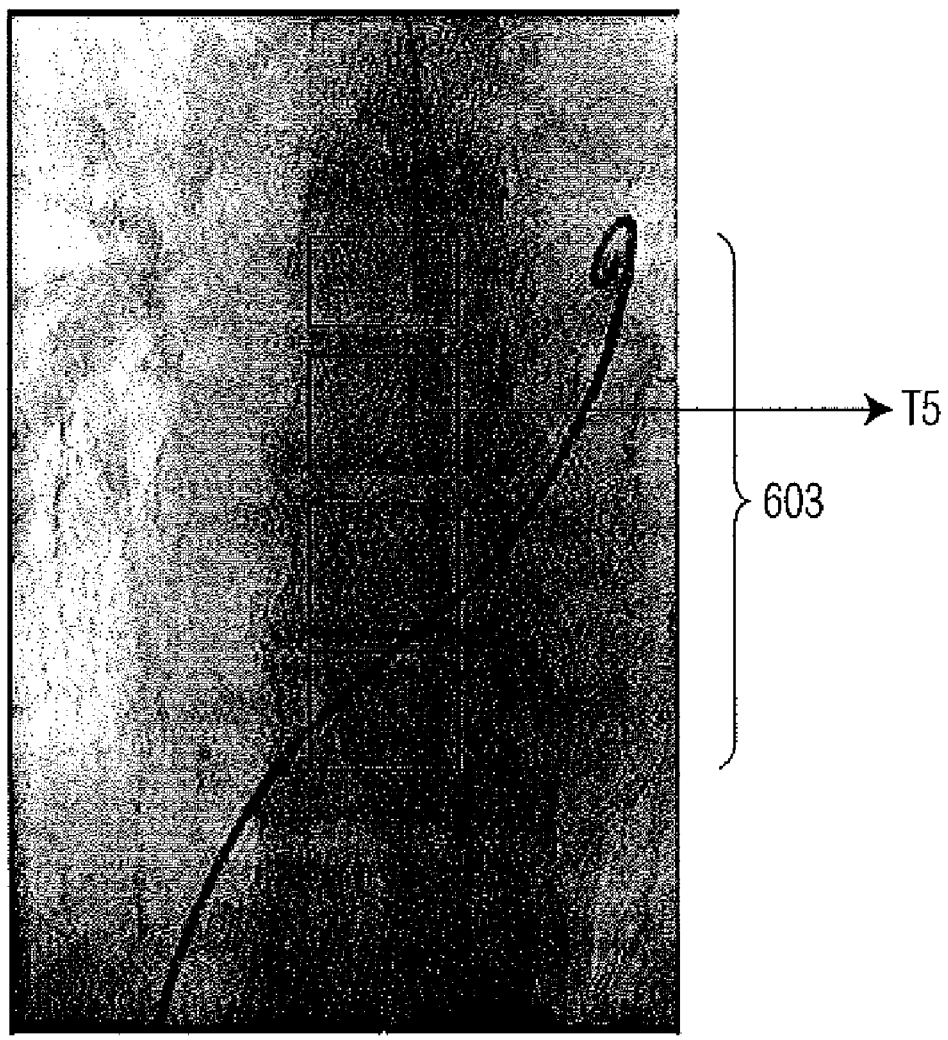
FIG. 7 shows a cardiac image including vertebrae and vertebrae overlay graphic elements for an anterior-posterior position after alignment of the overlay elements, according to invention principles.
Figure 10:
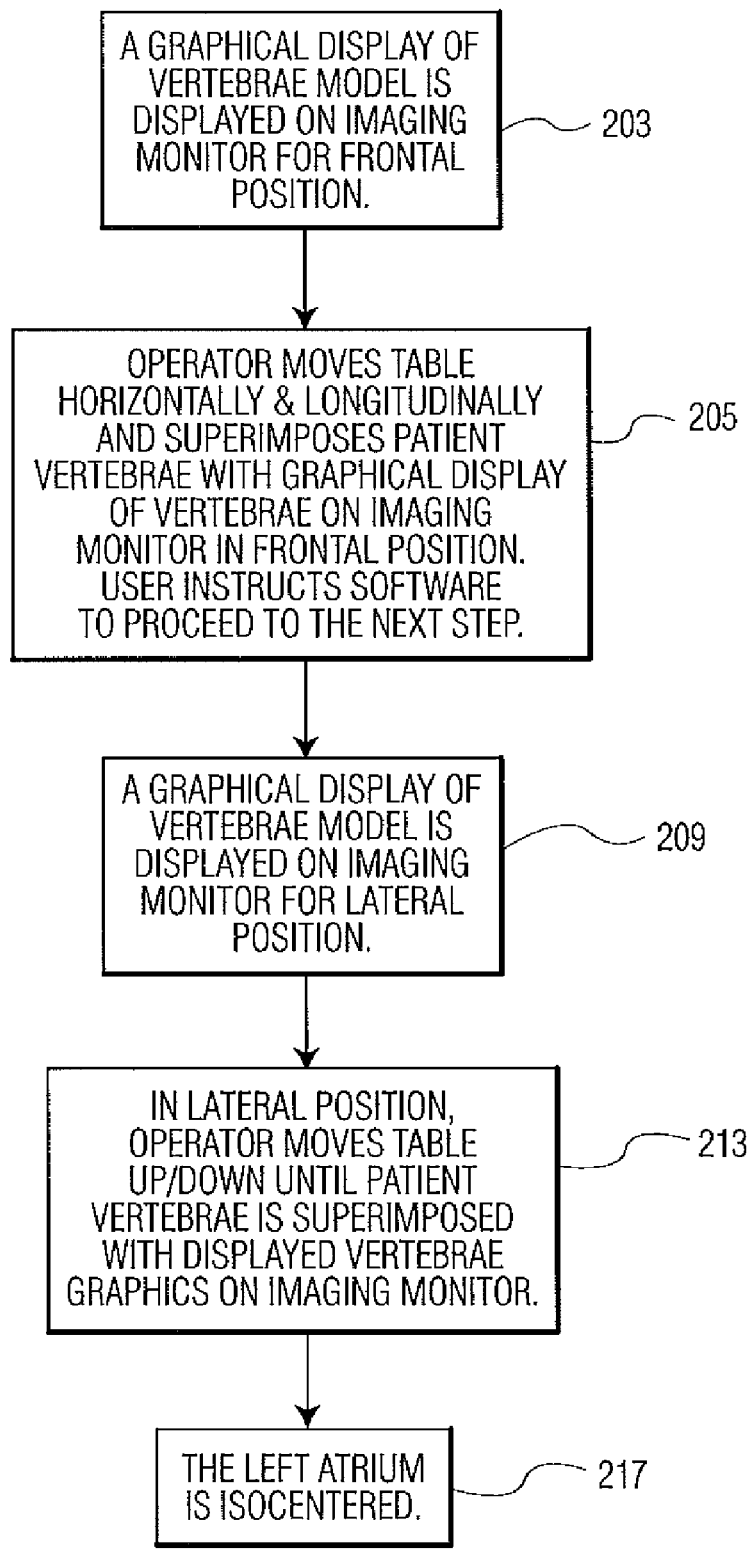
FIG. 10 shows a flowchart of a process for centering of a Left Atrium for imaging used by a system for positioning a patient for X-ray imaging of a Left Atrium of a heart, according to invention principles.
Figure 15:
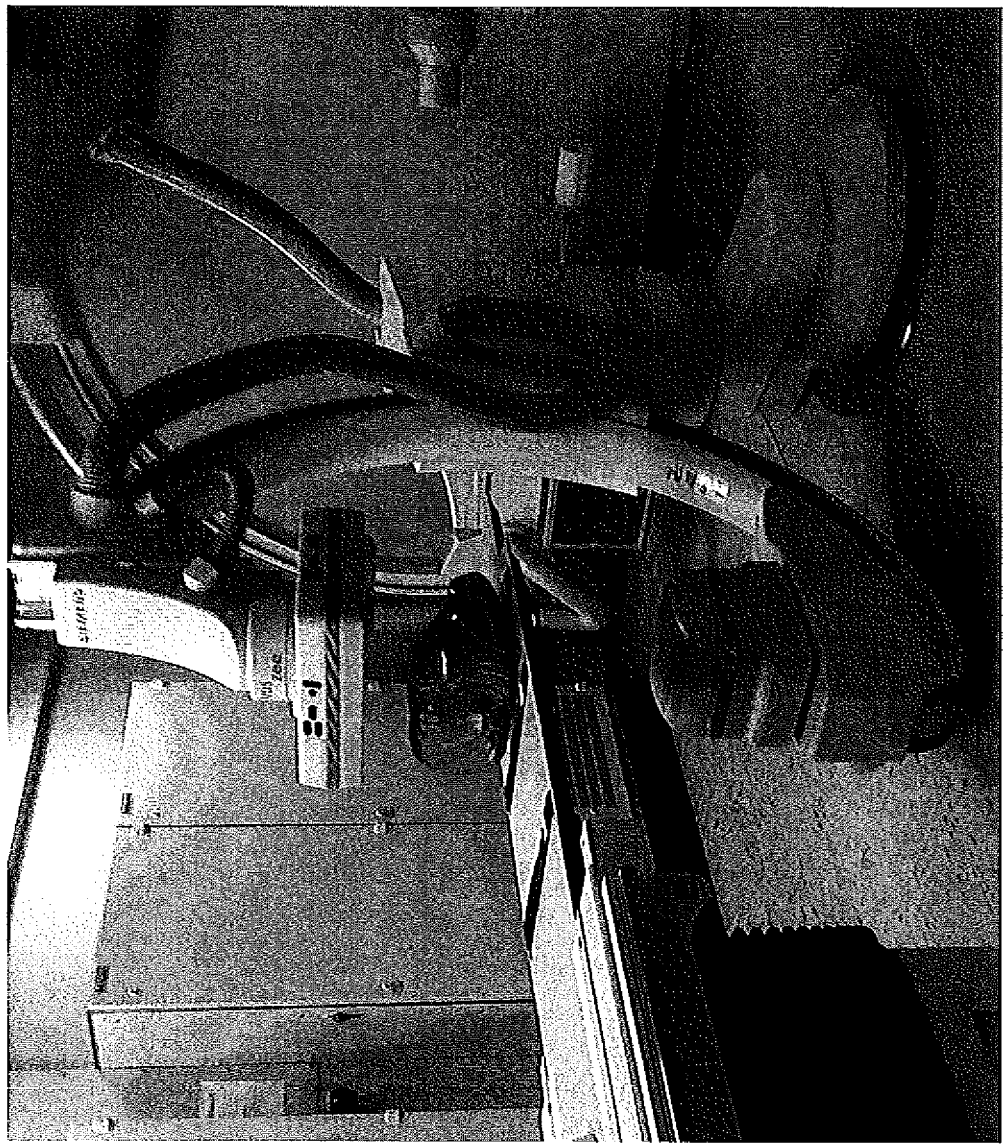
FIG. 15 shows an X-ray imaging system including a rotatable C-arm mounting a radiation emitter and detector at opposite C-arm ends in a frontal position.

FIG. 10 shows a flowchart of a process for centering of a Left Atrium for imaging used by system 10 (FIG. 5) for positioning a patient for X-ray imaging of a Left Atrium of a heart. FIG. 15 shows X-ray imaging system 25 including a rotatable C-arm mounting a radiation emitter and detector at opposite C-arm ends positioned for patient frontal (anterior-posterior) imaging. In step 203 system 10 superimposes a vertebrae overlay on a cardiac image acquired using system 25 in a patient frontal (anterior-posterior) position. FIG. 1 shows orientation of a vertebral column on a patient body surface and FIGS. 2 and 3 show a Vertebral Column. FIG. 6 shows a cardiac image acquired by system 25 and including vertebrae and vertebrae graphic overlay element 603 for an anterior-posterior position and superimposed onto the cardiac image by display processor 15 prior to alignment of the overlay elements. Graphic overlay element 603 identifies the T5 vertebra (and other vertebra in other embodiments) facilitating image and alignment review. In step 205, a user of system 25 horizontally and longitudinally moves the patient support table shown in FIG. 15 until overlay 603 is superimposed over the corresponding patient vertebrae in the cardiac image. The adjustment of the table is done manually by the operator to move the table to match the patient vertebrae with the overlay graphics. FIG. 7 shows a cardiac image presented on display 19 including vertebrae and vertebrae overlay graphic elements 603 for an anterior-posterior position after alignment of the overlay elements with the patient vertebrae.

Figure 8:
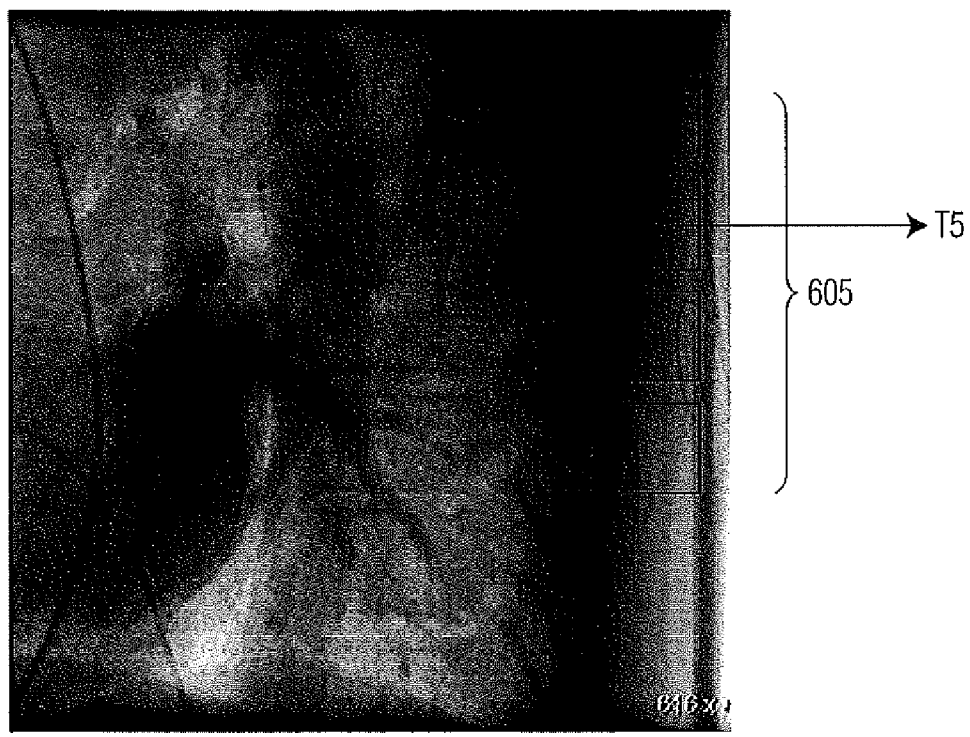
FIG. 8 shows a cardiac image including vertebrae and overlay graphic elements for a lateral position prior to alignment of the overlay elements, according to invention principles.
Figure 9:
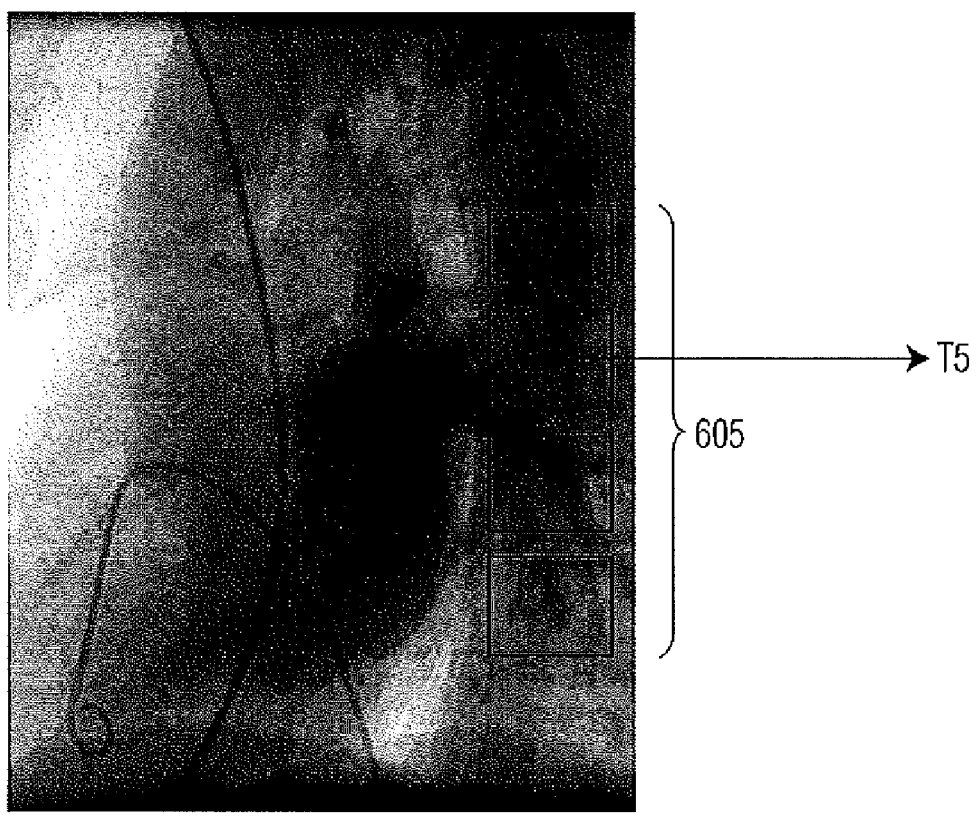
FIG. 9 shows a cardiac image including vertebrae and vertebrae overlay graphic elements for a lateral position after alignment of the overlay elements, according to invention principles.
Figure 16:
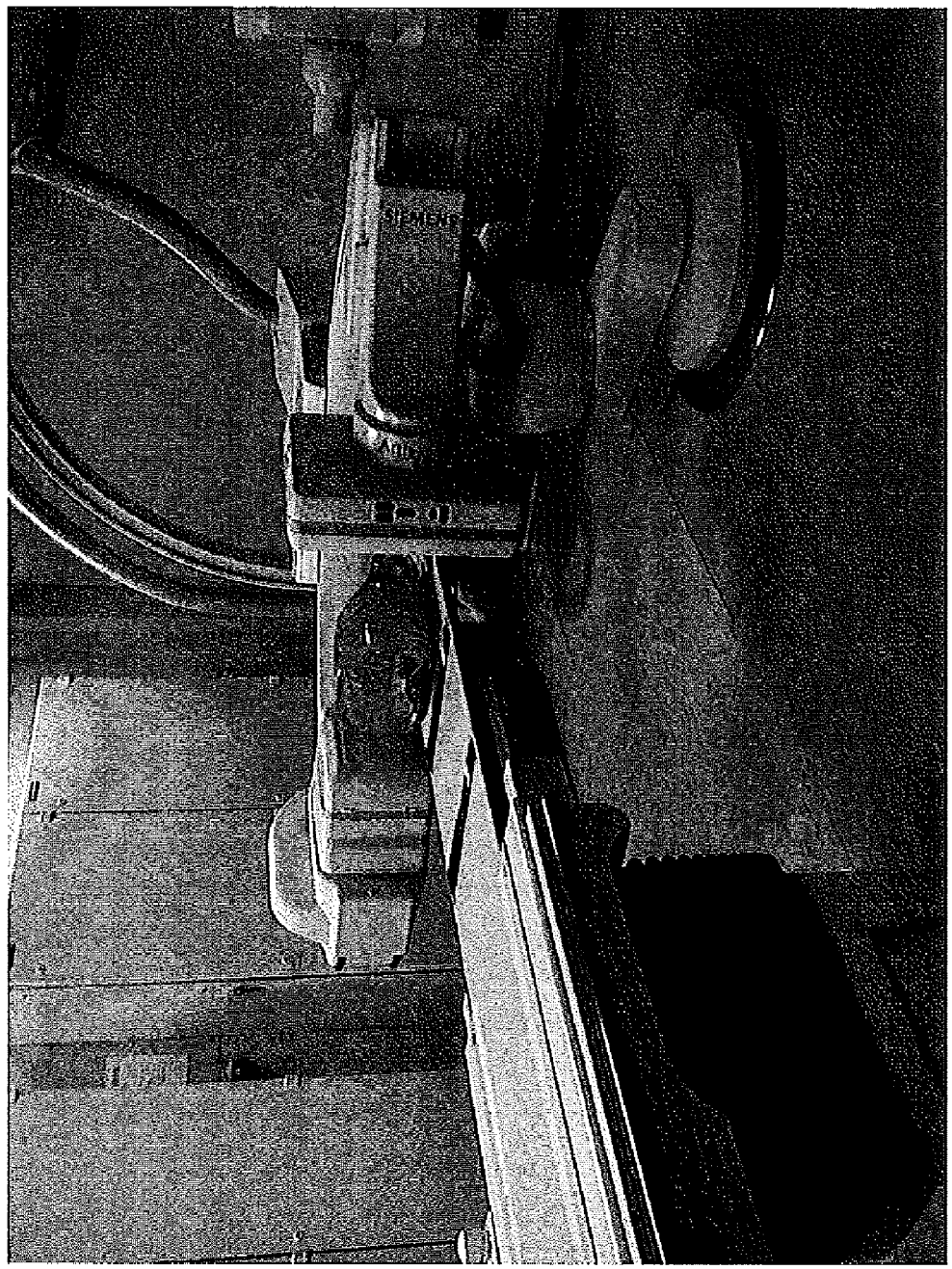
FIG. 16 shows an X-ray imaging system including a rotatable C-arm mounting a radiation emitter and detector at opposite C-arm ends in a lateral position.

FIG. 16 shows X-ray imaging system 25 including a rotatable C-arm mounting a radiation emitter and detector at opposite C-arm ends positioned for patient lateral imaging. In step 209 system 10 superimposes a vertebrae overlay on a cardiac image acquired using system 25 in a patient lateral position. FIG. 8 shows a cardiac image acquired by system 25 and including vertebrae and vertebrae graphic overlay element 605 for a lateral position and superimposed by display processor 15 onto the cardiac image prior to alignment of the overlay elements. Graphic overlay element 605 identifies the T5 vertebra (and other vertebra in other embodiments) facilitating image and alignment review. In step 213, the user of system 25 vertically raises or lowers the patient support table shown in FIG. 16 until overlay 605 is superimposed over the corresponding patient vertebrae in the cardiac image. FIG. 9 shows a cardiac image presented on display 19 including vertebrae and vertebrae overlay graphic elements 605 for a lateral position after alignment of the overlay elements with the patient vertebrae. In step 217 the left atrium of the cardiac images is iso-centered. System 10 advantageously guides a user in iso-centering the left atrium and is used to position the left atrium at iso-center of the angiography system for acquiring a 3D image of the left atrium with rotational angiography system 25.

Figure 4:
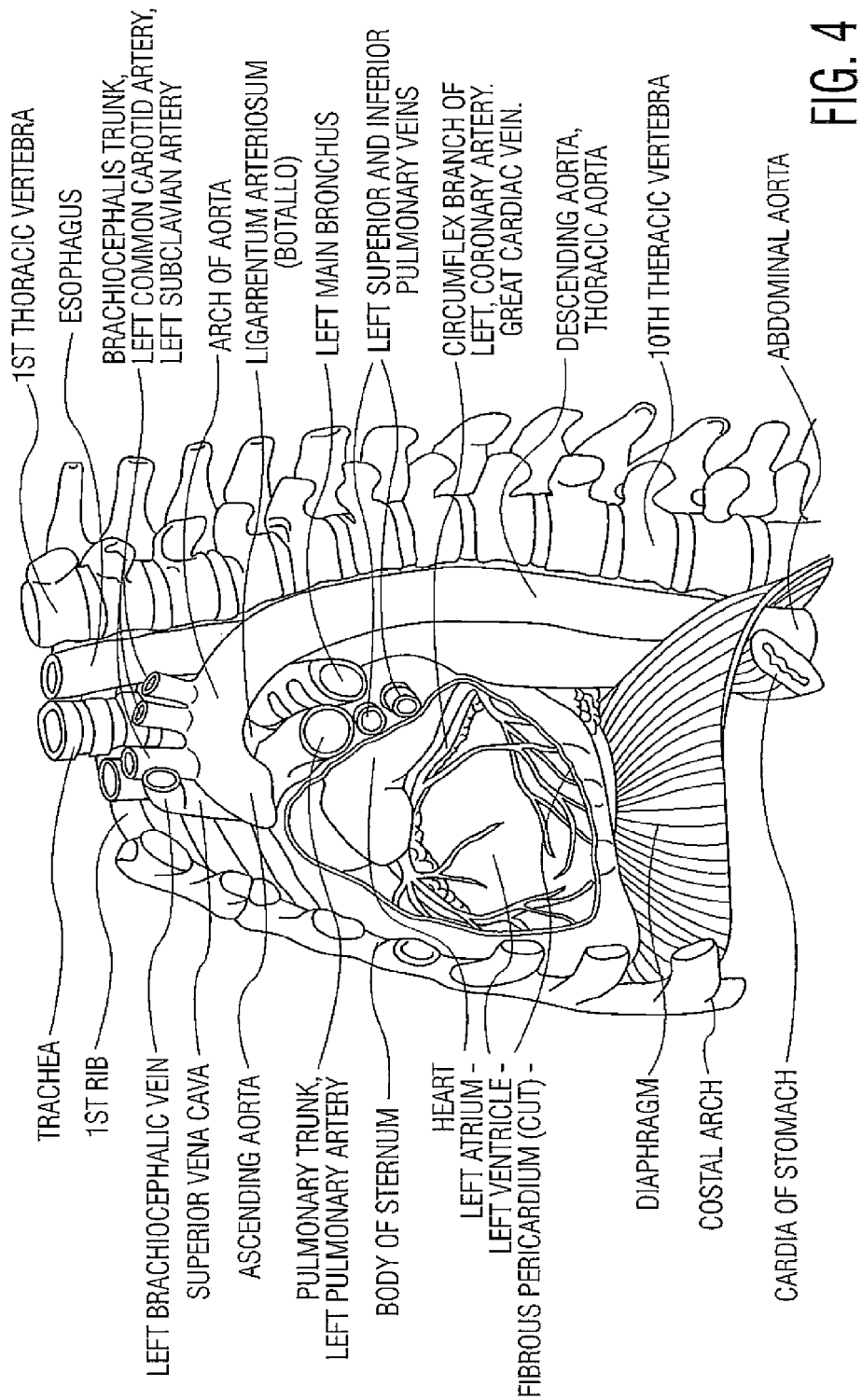
FIG. 4 shows Thoracic Viscera.
Figure 11:
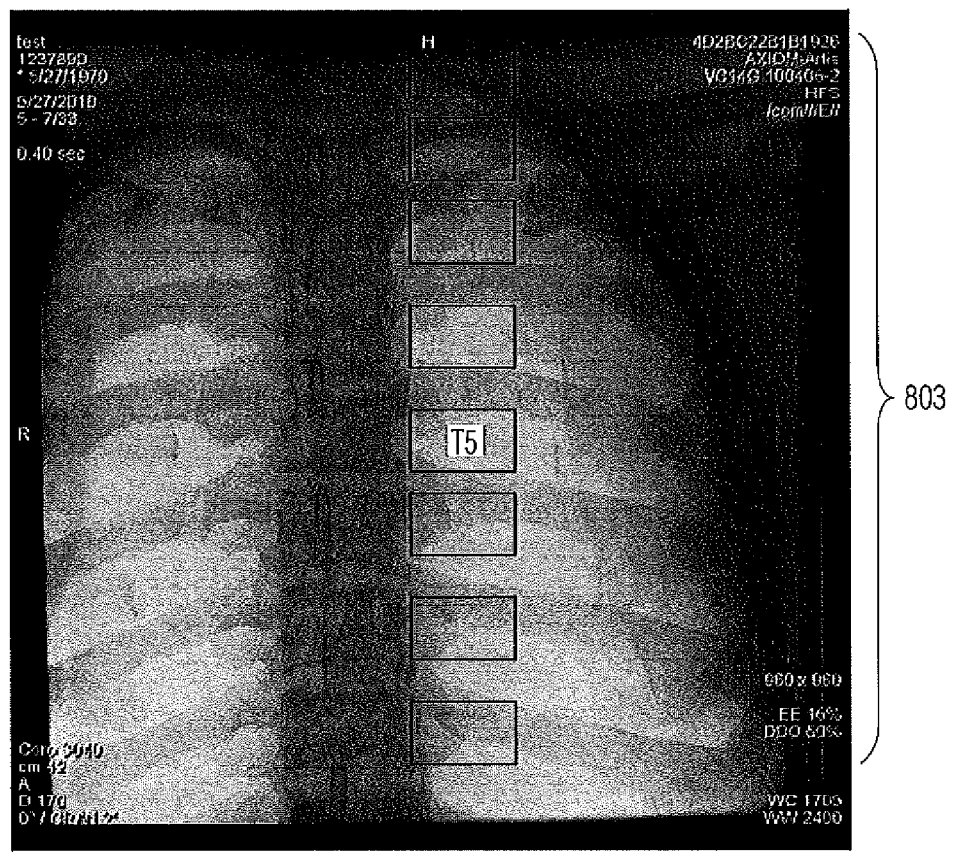
FIG. 11 shows a thoracic phantom image including vertebrae and vertebrae overlay graphic elements for an anterior-posterior position prior to alignment of the overlay elements, according to invention principles.
Figure 12:
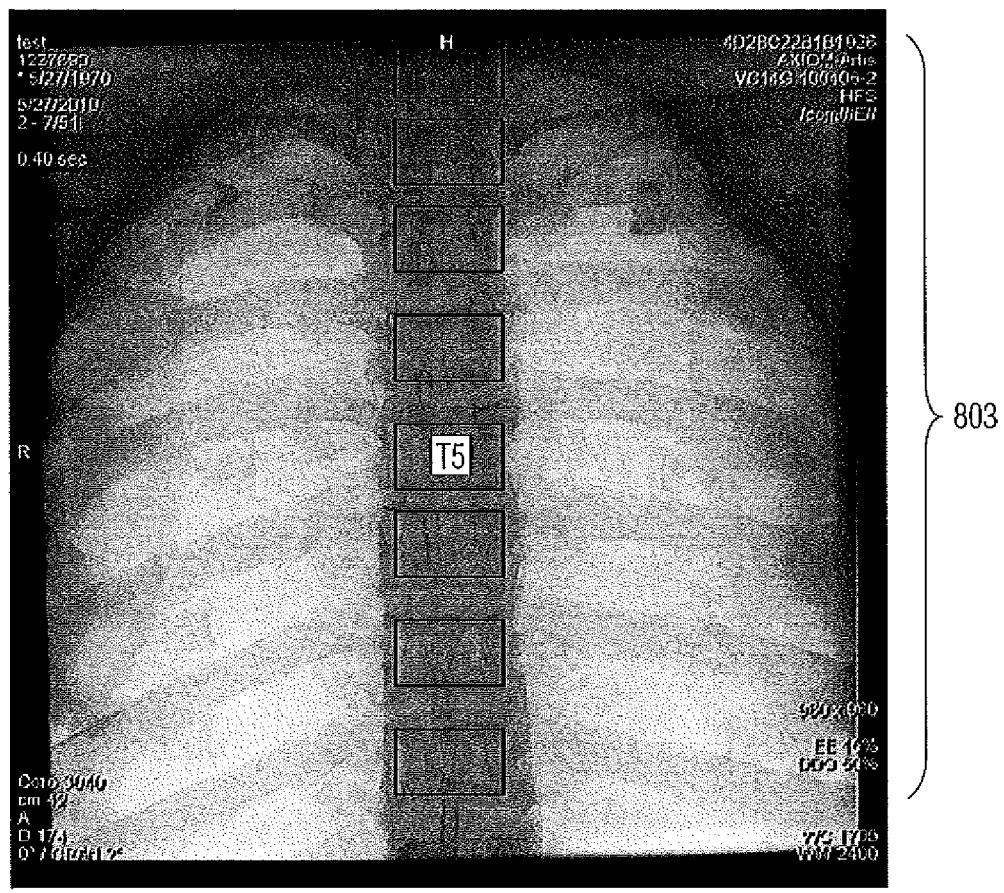
FIG. 12 shows a thoracic phantom image including vertebrae and vertebrae overlay graphic elements for an anterior-posterior position after alignment of the overlay elements, according to invention principles.

FIGS. 11-14 illustrate iso-centering of thoracic vertebrae similar to the iso-centering of a cardiac left atrium described in connection with FIGS. 6-9. An overlay such as a thoracic vertebrae overlay, is adaptively selected for a particular set of demographic characteristics of a subject patient, from multiple different overlays associated with corresponding patient populations having particular demographic characteristics such as one or more of age, weight, gender, height and pregnancy status. FIG. 4 shows Thoracic Viscera. System 10 superimposes a vertebrae overlay on a thoracic image acquired using system 25 in a patient frontal (anterior-posterior) position. FIG. 11 shows a thoracic image acquired by system 25 and including vertebrae and vertebrae graphic overlay element 803 for an anterior-posterior position and superimposed by display processor 15 onto the thoracic image prior to alignment of the overlay elements. Graphic overlay element 803 identifies the T5 vertebra (and other vertebrae in other embodiments) facilitating image and alignment review. A user of system 25 horizontally and longitudinally moves the patient support table shown in FIG. 15 until overlay 803 is superimposed over the corresponding patient vertebrae in the thoracic image. The adjustment of the table is done manually by the operator to move the table to match the patient vertebrae with the overlay graphics. FIG. 12 shows a thoracic image presented on display 19 including vertebrae and vertebrae overlay graphic elements 803 for an anterior-posterior position after alignment of the overlay elements with the patient vertebrae.

Figure 13:
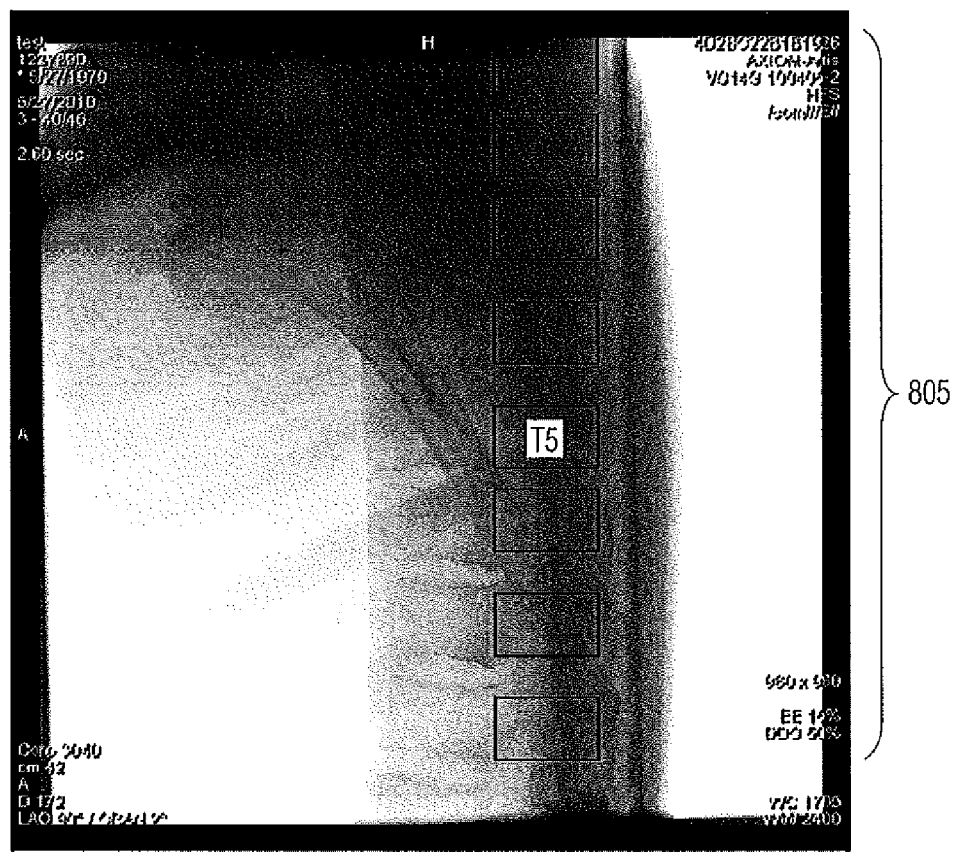
FIG. 13 shows a thoracic phantom image including vertebrae and vertebrae overlay graphic elements for a lateral position prior to alignment of the overlay elements, according to invention principles.
Figure 14:
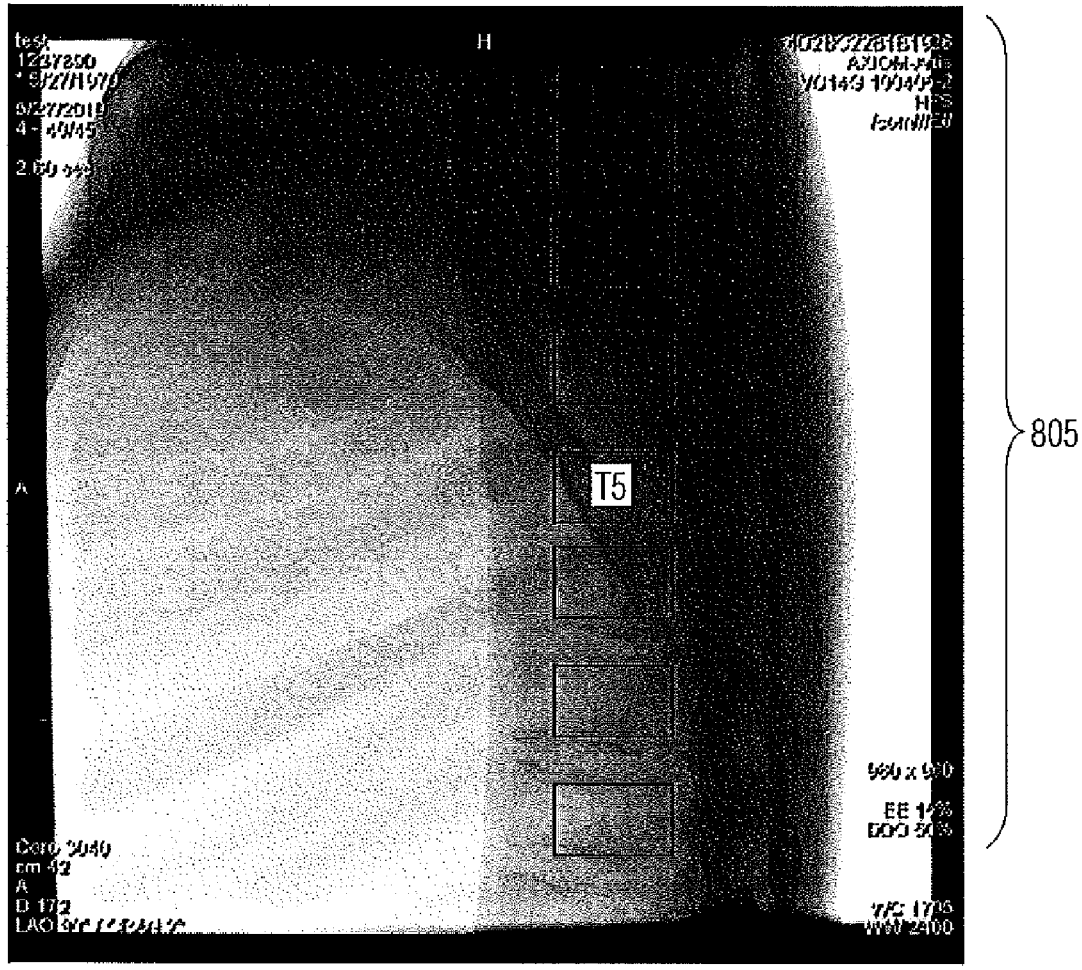
FIG. 14 shows a thoracic phantom image including vertebrae and vertebrae overlay graphic elements for a lateral position after alignment of the overlay elements, according to invention principles.

System 10 superimposes a vertebrae overlay on a thoracic image acquired using system 25 in a patient lateral position. FIG. 13 shows a thoracic image acquired by system 25 and including vertebrae and vertebrae graphic overlay element 805 for a lateral position and superimposed by display processor 15 onto the thoracic image prior to alignment of the overlay elements. Graphic overlay element 805 identifies the T5 vertebra (and other vertebra in other embodiments) facilitating image and alignment review. A user of system 25 vertically raises or lowers the patient support table shown in FIG. 16 until overlay 805 is superimposed over the corresponding patient vertebrae in the thoracic image. FIG. 14 shows a thoracic image presented on display 19 including vertebrae and vertebrae overlay graphic elements 805 for a lateral position after alignment of the overlay elements with the patient vertebrae. Thereby the vertebrae in the thoracic images are iso-centered. System 10 advantageously guides a user in iso-centering thoracic vertebrae for acquiring a 3D image of the thoracic region with system 25.

Figure 17:
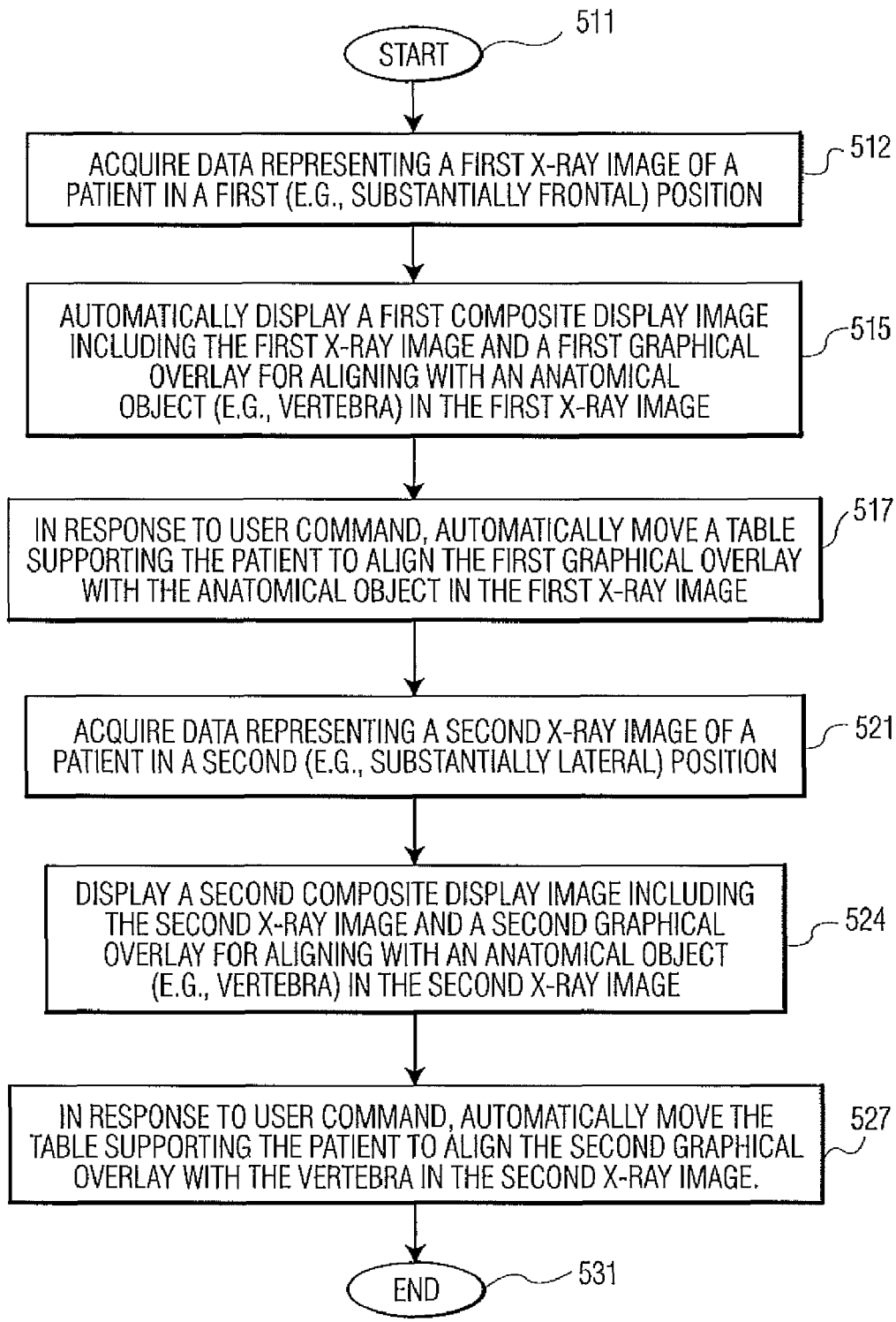
FIG. 17 shows a flowchart of a process used by a system for positioning a patient for X-ray imaging of a Left Atrium of a heart, according to invention principles.

FIG. 17 shows a flowchart of a process used by system 10 (FIG. 5) for positioning a patient for X-ray imaging of an anatomical feature (e.g., a Left Atrium of a heart or thoracic region). In step 512, following the start at step 511, imaging system 25 (FIG. 5) acquires data representing a first X-ray image of a patient in a first (e.g., a substantially frontal) position. Imaging system 25 includes an arm rotatable about the patient including a radiation emitter and a radiation detector positioned on substantially opposite sides of the patient. In one embodiment the imaging system acquires the data representing the first X-ray image with the radiation detector substantially above the patient lying on his back on the table. Display processor 15 in step 515 automatically displays on display 19 a first composite display image including the first X-ray image and a first graphical overlay for aligning with an anatomical object (e.g., vertebra) in the first X-ray image. Imaging system 25 in step 517 in response to user command, moves a table supporting the patient (e.g., in a substantially horizontal direction) to align the first graphical overlay with the anatomical object in the first X-ray image.

In step 521 imaging system 25 acquires data representing a second X-ray image of a patient in a second (e.g., a substantially lateral) position. In one embodiment imaging system acquires the data representing the second X-ray image with the radiation detector substantially to the side of the patient lying on his back on the table. Display processor 15 in step 524 automatically displays a second composite display image including the second X-ray image and a second graphical overlay for aligning with an anatomical object (e.g., vertebra) in the second X-ray image. Imaging system 25 in step 527 in response to user command, moves the table supporting the patient (e.g., in a substantially vertical direction) to align the second graphical overlay with the anatomical object in the second X-ray image. In one embodiment, imaging system 25 is positioned for imaging a heart left atrium (by iso-centering the left atrium) in response to substantially horizontal movement of the table supporting the patient to align the first graphical overlay with the vertebra in the first X-ray image and in response to substantially vertical movement of the table supporting the patient to align the second graphical overlay with the vertebra in the second X-ray image. Display processor 15 selects the first graphical overlay from multiple different overlays associated with different patients having different demographic characteristics in response to data indicating a demographic characteristic of the patient. The demographic characteristics comprise at least one of, (a) height, (b) weight, (c) gender and (d) age. Display processor 15 selects the second graphical overlay from multiple different overlays associated with different patients having different demographic characteristics in response to data indicating a demographic characteristic of the patient. The process of FIG. 17 terminates at step 531.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 5-17 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system superimposes adaptively selected graphic overlays of anatomical objects over images acquired in different orientations (frontal and lateral, for example) enabling a user to move a patient via patient table adjustment to move the overlays to align with corresponding anatomical features and thereby center an anatomical object for imaging. Further, the processes and applications may, in alternative embodiments, be located on one or more (e.g., distributed) processing devices on a network linking the units of FIG. 5. Any of the functions and steps provided in FIGS. 5-17 may be implemented in hardware, software or a combination of both.

What is claimed is:

1. A system for positioning a patient for X-ray imaging of a Left Atrium of a heart, comprising:
an imaging system for,
acquiring data representing a first X-ray image of a patient in a substantially frontal position and
acquiring data representing a second X-ray image of a patient in a substantially lateral position;
a display processor for initiating generation of data representing,
a first composite display image including said first X-ray image and a first graphical overlay for aligning with vertebra in said first X-ray image and
a second composite display image including said second X-ray image and a second graphical overlay for aligning with vertebra in said second X-ray image and said imaging system is positioned for imaging a heart left atrium in response to movement of a table supporting said patient to align said first graphical overlay with said vertebra in said first X-ray image and to align said second graphical overlay with said vertebra in said second X-ray image.

2. A system according to claim 1, wherein
said imaging system is positioned for imaging a heart left atrium in response to substantially horizontal movement of said table supporting said patient to align said first graphical overlay with said vertebra in said first X-ray image and in response to substantially vertical movement of said table supporting said patient to align said second graphical overlay with said vertebra in said second X-ray image.

3. A system according to claim 1, wherein
said imaging system includes an arm rotatable about said patient including a radiation emitter and a radiation detector positioned on substantially opposite sides of the patient,
said imaging system acquires said data representing said first X-ray image with said radiation detector substantially above said patient lying on his back on said table and
said imaging system acquires said data representing said second X-ray image with said radiation detector substantially to the side of said patient lying on his back on said table.

4. A system according to claim 1, wherein
said display processor selects said first graphical overlay from a plurality of different overlays associated with different patients having different demographic characteristics in response to data indicating a demographic characteristic of said patient.

5. A system according to claim 4, wherein
said demographic characteristics comprise at least one of, (a) height, (b) weight, (c) gender and (d) age.

6. A system according to claim 4, wherein
said display processor selects said second graphical overlay from a plurality of different overlays associated with different patients having different demographic characteristics in response to data indicating a demographic characteristic of said patient.

7. A system according to claim 1, wherein
said imaging system is positioned for imaging a heart left atrium by iso-centering the left atrium.

8. A method for positioning a patient for X-ray imaging of a Left Atrium of a heart, comprising the activities of:
acquiring data representing a first X-ray image of a patient in a substantially frontal position;
displaying a first composite display image including said first X-ray image and a first graphical overlay for aligning with vertebra in said first X-ray image;
in response to user command, moving a table supporting said patient to align said first graphical overlay with said vertebra in said first X-ray image;
acquiring data representing a second X-ray image of a patient in a substantially lateral position;
displaying a second composite display image including said second X-ray image and a second graphical overlay for aligning with vertebra in said second X-ray image; and
in response to user command, moving said table supporting said patient to align said second graphical overlay with said vertebra in said second X-ray image.

9. A system according to claim 8, wherein
said activity of moving said table supporting said patient to align said first graphical overlay with said vertebra in said first X-ray image comprises moving said table in a substantially horizontal direction.

10. A system according to claim 9, wherein
said activity of moving said table supporting said patient to align said second graphical overlay with said vertebra in said second X-ray image comprises moving said table in a substantially vertical direction.

11. A system for positioning a patient for X-ray imaging of an anatomical feature, comprising:
an imaging system for,
acquiring data representing a first X-ray image of a patient in a first position and
acquiring data representing a second X-ray image of a patient in a different second position;
a display processor for initiating generation of data representing,
a first composite display image including said first X-ray image and a first graphical overlay for aligning with an anatomical object in said first X-ray image and
a second composite display image including said second X-ray image and a second graphical overlay for aligning with an anatomical object in said second X-ray image and said imaging system is positioned for imaging an anatomical feature in response to movement of a table supporting said patient to align said first graphical overlay with said anatomical object in said first X-ray image and to align said second graphical overlay with said anatomical object in said second X-ray image.

12. A system according to claim 11, wherein
said imaging system is positioned for imaging said anatomical feature in response to substantially horizontal movement of said table supporting said patient to align said first graphical overlay with said anatomical object in said first X-ray image and in response to substantially vertical movement of said table supporting said patient to align said second graphical overlay with said anatomical object in said second X-ray image.

13. A system according to claim 11, wherein
said anatomical feature is a heart.

14. A system according to claim 13, wherein
said imaging system is positioned for imaging a heart left atrium by iso-centering the left atrium.

* * * * *